Feb. 25, 1969 E. S. BOERNER Plant Pat. 2,866
CHRYSANTHEMUM PLANT
Filed Aug. 3, 1967
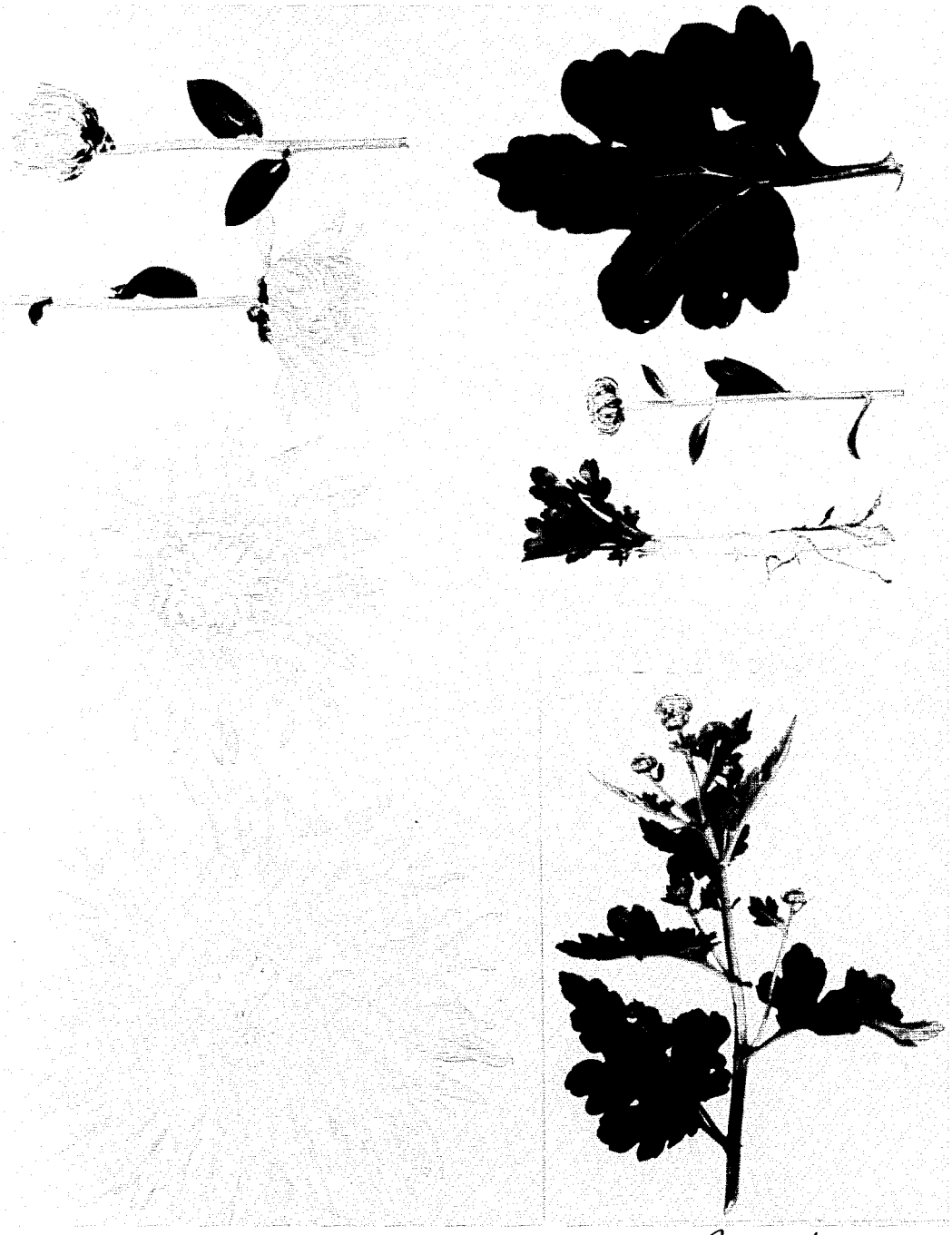
Inventor.
E. S. Boerner, Deceased
By: Lincoln Rochester Trust Company
By: Edward L. Jenner, Trust Officer
and Roger L. Boerner
By: Robbs & Robb, Executors.
Attorneys.

United States Patent Office

Plant Pat. 2,866
Patented Feb. 25, 1969

2,866
CHRYSANTHEMUM PLANT

Eugene S. Boerner, deceased, late of Benton, N.Y., by Lincoln Rochester Trust Company, Rochester, N.Y., and Roger L. Boerner, Milwaukee, Wis., executors, assignor to Jackson & Perkins Company, Newark, N.Y., a corporation of New York Filed Aug. 3, 1967, Ser. No. 658,297
U.S. Cl. Plt.—78 1 Claim
Int. Cl. A01h 5/02

The present invention relates to a new and distinct variety of chrysanthemum plant of the thick decorative class, which was originated by the late Eugene S. Boerner, deceased, by crossing the chrysanthemum variety known as "Golden Scepter" (unpatent) with the variety known as "Yellow Seagull" (Plant Patent No. 1,547).

The primary objective of this breeding was to produce a new and improved chrysanthemum variety having a flower size and double petalage comparable to the flowers of "Golden Scepter," combined with the hardiness and vigor of "Yellow Seagull." This objective was fully achieved, along with other desirable improvements, as evidenced by the following unique combination of characteristics which are outstanding in the new variety and which distinguish it from its parents, as well as from all other chrysanthemum varieties:

(1) a hardy and free habit of growth;
(2) A large and thick decorative bloom form;
(3) A very double flower petalage; and
(4) A distinctive and attractive general color tonality of the flowers corresponding to Apricot Yellow, very lightly overcast with Light Cadmium.

Asexual reproduction of the new variety by both top cuttings and underground runners, as performed at Newark, N.Y., shows that the foregoing characteristics and distinctions come true to form and are established and transmitted through succeeding propagations.

The accompanying drawing shows typical specimens of the vegetative growth and flowers of the new chrysanthemum variety in different stages of development and as depicted in color as nearly true as it is reasonably possible to make the same in a color illustration of this character, as well as a typical specimen stem which illustrates the form and habit of growth of the plant.

The following is a detailed description of the new variety, with color terminology in accordance with Ridgeway's Color Standards and Nomenclature:

Parentage: Seedling.
*Seed parent.*—"Golden Scepter."
*Pollen parent.*—"Yellow Seagull."
Classification: Thick decorative.
Growth: From 18 inches to 24 inches tall.
Location where grown and observed: Outdoors at Newark, N.Y. near the middle of the month of October.

Cold resistance: Winter hardy in northern New York State.
Blooming period: In the Newark, N.Y. climatic area, blooming begins in early September and continues until frost.

*Flower*

Bud:
*Color.*—When petals first divide—Pinard Yellow, Plate 4, with tips of petals Light Coral, Plate 13. When petals begin to unfurl—Mustard Yellow, Plate 16, lightly overcast with Ferruginous, Plate 14, in the lower half of the petal. When half-blown: inside—Deep Chrome, Plate 3; outside—Apricot Yellow, Plate 4.
*Peduncle.*—Color—Deep Chrysolite Green, Plate 31. Strength—strong.

Bloom:
*Size.*—Five inches.
*Stem.*—Stiff.
*Form.*—Thick decorative.
*Petalage.*—Very double.
*Color.*—Center of flower—Light Cadmium, Plate 4. Outer petals—Apricot Yellow, Plate 4. Base of petals—Pale Greenish-Yellow, Plate 5. Inside of petals—Apricot Yellow, Plate 4, very lightly overcast with Light Cadmium, Plate 4. Reverse of petals—Buff-Yellow, Plate 4.
*Petals.*—Texture—crisp. Form—oval.
*Fragrance.*—Characteristic chrysanthemum.

*Plant*

Form: Upright; branching.
Growth: Free.
Foliage:
*Size.*—From large to very large.
*Quantity.*—Normal.
*Color.*—Upper side—Dark Cress Green, Plate 31. Reverse side—Cress Green, Plate 31.
*Texture.*—Very thick.

What is claimed is:

1. A new and distinct variety of chrysanthemum plant of the thick decorative class, substantially as herein shown and described, characterized particularly as to novelty by the unique combination of a hardy and free habit of growth, a large bloom size, a very double flower petalage, and a distinctive and attractive general color tonality of the flowers corresponding to Apricot Yellow, very lightly overcast with Light Cadmium.

No references cited.

ROBERT E. BAGWILL, *Primary Examiner.*